United States Patent [19]

Balme

[11] 3,975,401

[45] Aug. 17, 1976

[54] PROCESS FOR THE DEHYDRATION OF BIS-MALEAMIC ACIDS

[75] Inventor: Maurice Balme, Sainte-Foy-les-Lyon, France

[73] Assignee: Rhone-Poulenc S.A., Paris, France

[22] Filed: Sept. 28, 1973

[21] Appl. No.: 401,603

[30] Foreign Application Priority Data
Oct. 2, 1972    France ............................ 72.34822

[52] U.S. Cl. .............................. 260/326.26; 260/691
[51] Int. Cl.$^2$ ........................................ C07D 207/44
[58] Field of Search ............................... 260/326.26

[56] References Cited
UNITED STATES PATENTS

| | | | |
|---|---|---|---|
| 3,018,290 | 1/1962 | Sauers | 260/326.25 |
| 3,148,196 | 9/1964 | Ladd | 260/518 R |
| 3,627,780 | 12/1971 | Bonnard et al. | 260/326.26 |
| 3,839,358 | 10/1974 | Bargain | 260/326.26 |

Primary Examiner—Alton D. Rollins
Assistant Examiner—Mark L. Berch
Attorney, Agent, or Firm—Stevens, Davis, Miller & Mosher

[57] ABSTRACT

An improved process for the dehydration of bis-maleamic acids to bis-maleimides is provided which comprises heating the bis-maleamic acid with a lower carboxylic acid anhydride in acetone, in the presence of 0.2 to 1 mol of tertiary amine per mol of bis-maleamic acid and of a soluble nickel derivative and 0.1 to 10 mols of water per mol of bis-maleamic acid and precipitating the resulting bis-maleimide by the addition of water. The addition of water to the starting materials reduces the proportion of by-products produced and increases the degree of cyclodehydration.

4 Claims, No Drawings

PROCESS FOR THE DEHYDRATION OF BIS-MALEAMIC ACIDS

The present invention relates to improvements in the dehydration of bis-maleamic acids.

French Pat. No. 2,055,969 describes, in particular, a process for the preparation of bis-maleimides by dehyration of the corresponding bis-maleamic acids with a lower carboxylic acid anhydride, in an organic diluent, in the presence of 0.2 to 1 mol of tertiary amine per mol of bis-maleamic acid and of a catalyst consisting of a nickel derivative which is soluble in the liquid phase of the reaction mixture. It is stated that acetic anhydride, generally in amounts of the order of 2.1 to 3 mols per mol of bis-maleamic acid, is advantageously used as the dicarboxylic acid anhydride, and that weights of solvent representing 1 to 4 times the weight of maleamic acid employed are generally very suitable.

It is also mentioned in French Pat. No. 2,055,969 that, at the end of the operation, the bis-maleimide can be precipitated by adding a non-solvent such as water, and then isolated in accordance with the usual methods, the volume of water preferably representing from 0.5 to three times the volume of solvent employed. Finally the French patent states that it is possible to use, directly, the suspensions of bis-maleamic acids produced by reacting maleic anhydride with a diprimary diamine in the organic diluent provided for the dehydration operation.

The present invention relates to a process for the dehydration of bis-maleamic acids by heating with a lower carboxylic acid anhydride in acetone, in the presence of 0.2 to 1 mol of tertiary amine per mol of bis-maleamic acid and of a soluble nickel derivative, followed by precipitation of the bis-maleimide with any by-products formed, by adding water to the final reaction mixture. This process is characterised in that 0.1 to 10 mols of water per mol of bis-maleamic acid subjected to dehydration are added to the starting materials.

The incorporation of water into the starting material makes it possible to increase the proportion of bis-maleimide in the final product precipitated. Furthermore, this addition of water makes it possible, paradoxically, to increase the degree of cyclodehydration. The latter consequence constitutes a definite advantage in the production of polymers from the bis-maleimides when the latter involve compression moulding. In effect, in carrying out such moulding, it is desirable that the material to be shaped should possess the least possible amount of volatile products or of groups which are precursors of volatile products under the temperature conditions adopted. Now, the process according to the invention makes it possible considerably to reduce the proportion, in the final precipitated product, of maleamido-acid groups:

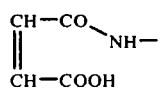

which are liable to liberate water during subsequent heating under pressure. Consequently, the final precipitated product can be used directly for numerous applications without it being necessary to subject it to a preliminary operation for the purpose of purifying the bis-maleimide formed.

The amount of water introduced at the start for the dehydration of the bis-maleamic acids is preferably from 0.15 to 5 mols per mol of bis-maleamic acid.

The advantages achieved by the process according to the invention are particularly marked when the volume of water added to the final reaction mixture for precipitating the product of dehydration represents from two to three times the volume of acetone used.

The bis-maleamic acids which can be subjected to the process according to the invention are those which are described in French Pat. No. 2,055,969. They include aliphatic, aromatic and heterocyclic bis-maleamic acids. This French Pat. No. 2,055,969 also gives the other conditions for carrying out the process in relation to the nature and the proportions of the tertiary amine and of the catalyst. Reference should be made to this French Patent for further details. By way of illustration, the reaction may be carried out generally at a temperature between 0° and 100°C, advantageously between 50° and 80°C and preferably at atmospheric pressure. Suitable tertiary amines include trialkylamines as well as the N,N-dialkylbenzylamines. Suitable nickel derivatives include nickel salts and divalent nickel complexes.

The following Examples further illustrate the present invention.

EXAMPLES 1 TO 6

A series of experiments is carried out, in each of which 0.2 g. of nickel acetate tetrahydrate, 4.75 g. of triethylamine, 25.5 g. of acetate anhydride and a weight $p$ of water are added, with stirring, to a suspension of 39.4 g. of bis-maleamic acid of the formula:

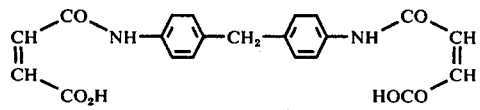

in 143 cm$_3$ (113 g.) of acetone.

The vessel containing the mixture is immersed in a fluid heated to 70°C; at the end of time $t$, a clear solution is obtained which is kept under these conditions for 80 minutes and then cooled to 4°C. 500 g. of water are added to the cooled solution and the solid which has precipitated is filtered off.

The results are given in Table A.

In this table, the following data are recorded: The weight $p$ of water introduced with the starting materials, the time $t$ at which the reaction mixture forms a clear solution, the ratio $r$ of the weight of solid product precipitated to the weight of bis-maleimide corresponding to the bis-maleamic acid employed, the proportion of $b$ of bis-maleimide in the precipitated product (by weight) and the quantity $m$ of maleamido-acid groups expressed as the number of molar milliequivalents per 100 g of precipitated product.

TABLE A

| Example No. | 1 | 2 | 3 | 4 | 5 | 6 |
|---|---|---|---|---|---|---|
| p (g) | 0.6 | 1.15 | 1.8 | 2.3 | 2.9 | 3.45 |
| t (mins.) | 11 | 14 | 9 | 10 | 7 | 9 |
| r (%) | 97.5 | 98 | 97.1 | 97 | 98.9 | 98.3 |
| b (%) | 80 | 82.4 | 85 | 83.1 | 81.4 | 80.7 |

TABLE A-continued

| Example No. | 1 | 2 | 3 | 4 | 5 | 6 |
|---|---|---|---|---|---|---|
| m | 9.04 | 8.65 | 7.59 | 6.75 | 8.34 | 10.85 |

By way of comparison when no water is introduced with the starting materials, the values obtained for $t$, $r$, $b$ and $m$, are, respectively, 20, 97.2, 77 and 15.75.

I claim:

1. In a process for the dehydration of a bis-maleamic acid by heating the bis-maleamic acid with a lower carboxylic acid anhydride in acetone, in the presence of 0.2 to 1 mol of tertiary amine per mol of bis-maleamic acid and of a soluble nickel derivative and precipitating the resulting bis-maleimide by the addition of water to the final reaction mixture, the improvement wherein 0.1 to 10 mols of water per mol of bis-maleamic acid are added to the bis-maleamic acid, lower carboxylic acid anhydride, acetone, tertiary amine and nickel derivative at the start of the reaction.

2. Process according to claim 1, the improvement in which the volume of water used to precipitate the product is from two to three times the volume of acetone used.

3. Process according to claim 1, the improvement in which 0.15 to 5 mols of water per mol of maleamic acid is used in the initial reaction mixture.

4. In a process for the dehydration of a bis-maleamic acid having the formula:

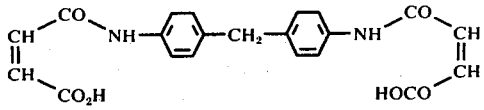

with acetic acid anhydride in acetone in the presence of 0.2 to 1 mol of triethylamine per mol of bis-maleamic acid and of nickel acetate and precipitating the resulting bis-maleimide by the addition of water to the final reaction mixture, the improvement wherein 0.1 to 10 mols of water per mol of bis-maleamic acid are added to the bis-maleamic acid, acetic acid anhydride, acetone, triethylamine and nickel acetate at the start of the reaction.

* * * * *